United States Patent [19]

Colon

[11] 4,400,566

[45] Aug. 23, 1983

[54] REDUCTION OF ORGANIC HALIDES

[75] Inventor: Ismael Colon, Middlesex, N.J.

[73] Assignee: Union Carbide Corporation, Danbury, Conn.

[21] Appl. No.: 361,192

[22] Filed: Mar. 24, 1982

Related U.S. Application Data

[63] Continuation-in-part of Ser. No. 302,691, Sep. 15, 1981, abandoned, which is a continuation of Ser. No. 199,383, Oct. 21, 1980, abandoned.

[51] Int. Cl.³ .......................... C07B 17/00; C07C 1/26
[52] U.S. Cl. ..................................... 585/359; 585/469; 585/352; 260/465 R; 260/389; 568/658; 568/814; 204/72
[58] Field of Search ................ 585/359, 469; 568/658, 568/814; 260/465 R

[56] References Cited

U.S. PATENT DOCUMENTS

| | | | |
|---|---|---|---|
| 2,288,580 | 6/1942 | Baehr | 585/359 |
| 3,015,680 | 1/1962 | Isler | 585/359 |
| 3,075,021 | 1/1963 | Luvisi et al. | 260/650 |
| 3,454,644 | 7/1969 | Deuhirst | 568/814 |
| 3,737,384 | 6/1973 | Sweeny et al. | 210/59 |
| 3,879,483 | 4/1975 | Vanlautem | 585/359 |
| 4,022,795 | 5/1977 | Bamfield et at. | 260/296D |

OTHER PUBLICATIONS

Water & Sewage Works, *Reductive Degradation*, p. 40, Jan. 1979 by K. H. Sweeny, Ph.D.

*Primary Examiner*—John F. Niebling
*Attorney, Agent, or Firm*—Bernard Francis Crowe

[57] ABSTRACT

Organic halides are reduced to a dechlorinated products with a catalyst mixture consisting essentially of a nickel compound, a triarylphosphine and a halide ion, in the presence of reducing means for maintaining nickel in the zero valent state.

22 Claims, No Drawings

REDUCTION OF ORGANIC HALIDES

This is a continuation-in-part of Ser. No. 302,691 filed Sept. 15, 1981, abandoned, which in turn is a continuation of Ser. No. 199,383 filed Oct. 21, 1980 abandoned.

BACKGROUND OF THE INVENTION

The invention pertains to a method of reducing organic halides and more particularly to the use of a nickel-triaryl phosphine, halide catalyst in conjunction with reducing means capable of maintaining the nickel in a zero valent state.

The hydrogenolysis of carbon-halogen bonds has been effected in the past by hydrogen in the presence of nickel or palladium (F. W. Neuman, N. B. Sommer, C. E. Kaslow, and R. L. Shriner, *Org. Syn.*, Coll. Vol., 3, 519, 1955; H. Kammerer, L. Horner, and H. Beck, *Chem. Ber.*, 91, 1376, 1958; C. K. Alden and D. I. Davies, *J. Chem. Soc.*, C, 700, 1968; M. G. Reinecke, *J. Org. Chem.*, 29, 299; D. A. Denton, F. J. McQuillin, and P. L. Simpson, *J. Chem. Soc.*, 5535, 1964), and by metal hydrides (R. O. Hutchins, D. Hoke, J. Keogh, and D. Koharski, *Tet Lett.*, 3495, 1969; H. M. Bell, C. W. Vanderslice, and A. Spehar, *Jr. Org. Chem.*, 34, 3923, 1969; E. L. Eliel, *J. Am. Chem Soc.*, 71, 3970, 1949; G. J. Karabatsos and R. L. Shone, *Jr. Org. Chem.*, 33, 619, 1968; R. A. Egli, *Helv. Chim. Aceta*, 51, 2090, 1968). The metal hydride technique suffers from the disadvantage that metal hydrides are not very selective and will reduce a large number of other functional groups in the substrates as well. Carbon-halogen bonds may also be reductively cleaved by reaction with metals in protonic solvents (P. A. Levene, *Org. Syn., Coll. Vol.* 2, 320, 1943; S. Gronowitz and T. Raznekiewicz, *Org. Syn.*, 44, 9, 1964; P. G. Gassman and J. L. Marshall, *Org. Syn.*, 48, 68, 1968; D. Bryce-Smith and B. J. Wakefield, *Org. Syn.*, 47, 103, 1967; C. F. Wilcox, Jr., and F. G. Zajacek, *Jr. Org. Chem.*, 29, 2209, 1964; C. E. Moppett and J. K. Sutherland, and *J. Chem. Soc.*, C, 3040, 1968), by treatment with chromium (II) salts (D. M. Singleton and J. K. Kochi, *J. Am. Chem. Soc.*, 89, 6547, 1967; 90, 1582, 1968; J. K. Kochi, D. M. Singleton, and L. J. Andrews, *Tetrahedron*, 24, 3503, 1968; R. E. Erickson and R. K. Holmquist, *Tet. Lett.*, 4209, 1969; J. K. Kochi and P. E. Macadlo, *J. Am. Chem. Soc.*, 88, 4094, 1966), and by electrolytic methods (A. J. Fry, M. A. Mitnick, and R. G. Reed, *J. Org. Chem.*, 35, 1232, 1979; J. L. Webb, C. K. Mann, and H. M. Walborsky, *J. Am. Chem Soc.*, 92, 2042, 1970; F. H. Covitz, *J. Am. Soc.*, 89, 5403, 1967; R. E. Erickson, R. Ammino, M. D. Scanlon, and G. Zon, *J. Am. Chem. Soc.*, 91, 1767, 1969; A. J. Fry and R. H. Moore, *J. Org. Chem.*, 33, 1283, 1968).

Although zinc in acidic media has been used alone to reduce organic halides, its use is usually limited to iodides and bromides. Chlorides such as chlorobenzene are not reduced by zinc in this system.

Nickel has been used previously to catalytically reduce alkyl and aryl halides when used in combination with either sodium borohydride (S.-T. Lin and J. A. Roth, *J. Org. Chem.*, 44, 309, 1979; W. H. Denis, Jr., W. J. Cooper, *Ventron Alembic*, 9, 4, 1977) or lithium aluminum hydride (E. C. Ashby and J. J. Lin, *J. Org. Chem.*, 43, 1263, 1978), but the procedures were not selective. Functional groups such as carbonyls, nitriles, and the like, did not survive the reaction conditions.

Reduction of aryl halides by zero-valent nickel compounds has been observed before (M. F. Semmelhack, P. M. Helquist, and L. D. Jones, *J. Am. Chem. Soc.*, 93, 5908, 1971; L. Cassar and M. Foa, *J. Organoment Chem.*, 51, 381, 1973). However, none of these prior art reductions with zero-valent nickel were carried out in a manner where the nickel was used in catalytic amounts.

It is therefore an object of this invention to provide a method for reducing aryl halides in a selective manner which does not reduce other functional groups in the substrate compound.

Another object of this invention is the provide a method of reducing aryl halides using zero-valent nickel in catalytic amounts.

A further object of this invention is to provide a method of detoxifying polychlorinated biphenyls by reducing them to biphenyl.

Other objects of this invention will become apparent to those skilled in the art upon a further reading of the specification.

SUMMARY OF THE INVENTION

A method of reducing organic halides free of nitro substituents has been developed which comprises contacting said organic halide in a solvent containing at least one protic solvent under an inert atmosphere with a catalytic amount of a catalyst mixture consisting essentially of:

(1) a nickel compound containing no radicals in which nitrogen and oxygen are bonded directly to each other;

(2) a triaryl phosphine having 6 to about 14 carbon atoms in each aryl moiety and (3) a halide ion, in the presence of reducing means for maintaining nickel in the zero valence state, at a temperature of up to about 250° C., wherein the ratio of gram atoms of halide ion to nickel and the ratio of triaryl phosphine to nickel are each at least about 0.1.

Suitable nickel compounds include nickel (II) compounds such as nickel halides, including nickel chloride, nickel bromide, nickel fluoride and nickel iodide; nickel sulfates including $NiSO_4$, $NiSO_4 \cdot 6H_2O$, $NiSO_4 \cdot 7H_2O$, and the like; nickel carbonates, such as $NiCO_3$, $2NiCO_3 \cdot 3Ni(OH)_2 \cdot 4H_2O$, and the like; nickel salts of organic acids having 1 to 18 carbon atoms, such as, nickel formate, nickel acetate, nickel organic complexes, such as, nickel acetylacetone, dicholoro-bis(triphenylphospine)-nickel (II), and the like; and nickel (O) compounds, such as bis(1,5-cyclooctadiene) nickel, tetrakis (triphenylphosphine) nickel, and the like.

The anion of the nickel compounds is unimportant for the purpose of this invention, but merely serves to provide nickel ion to the catalyst mixture, but it must not interfere with the reaction of the nickel compound with the ligand, triarylphosphine. The preferred anions are the halides.

The ratio of gram atoms of nickel to mols of organic halide can range from about 0.0001 to about 1 but is preferably in the range of about 0.01 to about 0.1.

The ratio of triphenylphosphine to nickel can range from about 0.1 to about 100 mols per gram atom of nickel with the preferred range being about 1 to about 10.

Halide ion is required to make the reduction process of this invention catalytic in nickel when Zn is used as the reducing means with the iodides and bromides being the preferred halide ion. The cation associated with the halide ion (sometimes called a gegen ion) is relatively unimportant for the purposes of this invention, but should be such as to allow for the compounds, as for example a salt of a metal used as the source of halide ion, to be soluble in the solvent used. The gram atoms of halide to nickel can range from about 0.1 to about 1000 with the preferred range being about 1 to 100.

Whether they are used alone or in conjunction with aprotic solvents, the required protic solvents are exemplified by such compounds as water, aliphatic alcohols free of ethylenic unsaturation, such as, methanol, ethanol, and the like having up to about 10 atoms and the like.

Preferred aprotic solvents include dipolar solvents such as, dimethylacetamide, dimethylformamide, dimethylsulfoxide, sulfolane, and the like.

Suitable triarylphosphines include triphenylphosphine, triphenylphosphine containing alkyl or alkoxy substitutents having up to about 8 carbon atoms, and unsubstituted or alkyl-, alkoxy substituted trinaphthyl phosphines, and the like.

Although temperatures of about $-77°$ to about $250°$ C. can be used, it is preferred to use the range of about $20°$ to about $80°$ C.

Pressure is not critical and so for economic reasons it is preferred to use atmospheric pressure although both super-atmospheric and sub-atmospheric pressures can be used if desired.

Although zinc is the preferred reducing means, other metals can be used such as magnesium and others having a higher reduction potential than nickel. One can also use electrolytic reducing means using the cathode of an electrical circuit to effect reduction with the anode isolated in another compartment through a salt bridge or other device well known to those skilled in the art. When the reduction is done electrolytically a lower potential is applied when the nickel catalyst is present than would be necessary for the reduction of aryl halides without the nickel complex.

No special equipment is required carrying out the reduction of the organic halides of this invention.

Exemplary organic halides which serve as substrates in the method of this invention include alkyl halides having up to about 18 carbon atoms, aryl halides containing up to about 14 carbon atoms, ethylenically unsaturated chlorinated hydrocarbons having up to about 18 carbon atoms, cycloaliphatic halides having up to about 16 carbon atoms, and the like. These organic halides can be substituted with various, substituents except for nitro substituents. These organic halides in general are those that react with zero-valent nickel.

The invention is further described in the examples which follow. All parts and percentages are by weight unless otherwise specified.

EXAMPLES 1–10

Each of the examples delineated in the following Table utilized the following charge: 0.13 grams (1 millimole) of $NiCl_2$, 1.5 grams (6 millimoles) of triphenylphosphine, 0.5 grams (3 millimoles) of NaI, and 2 grams (31 millimoles) of powdered zinc contained in a 50 ml flask. The flask in each case was sealed, evacuated and filled with nitrogen. The solvent or solvents (30 ml) were introduced by syringe and once the mixture had produced a red-brown catalyst, 20 millimoles of organic halide was introduced into the reaction mixture.

The Table contains, in addition to process variables, conversion figures to a reduced product as well as the conversion figures of a by-product which is a coupled product of the organic halide. As can be seen in some cases (cf. example 5) there were substantial amounts of coupled products. In examples 1 and 2 the ratio of reduction to coupled products can be seen to be dependent upon the water concentration employed. It is possible to eliminate coupling completely by using alcohol as the solvent as shown in example 6, but the reaction rate was much slower. When deuterium oxide was used in place of water, mass spectral analysis of the anisole produced in example 3 revealed that deuterium incorporation had taken place. This demonstrates that water ($D_2O$) was the reduction source and not the solvent (DMF).

EXAMPLE 11

The procedure described in Examples 1–10 was followed with 0.13 grams $NiCl_2$, 1.0 grams of NaI, 2.0 grams of triphenylphosphine, 5.0 grams of powdered zinc, 15 ml of dimethylformamide and 5 ml of methanol. After the contents of the 50 ml flask were maintained under an atmosphere of nitrogen, 1 ml of 1,2,4-trichlorobenzene was added via syringe and the mixture was reacted for 4 hours at 50° C. after which all of the trichlorobenzene was consumed and the reaction products were found to be:

| Benzene | 91.9% |
|---|---|
| Chlorobenzene | 4.4% |
| 1,2-dichlorobenzene | 0.2% |
| 1,4-dichlorobenzene | 3.5% |

TABLE

| Example | Organic Halide RX | Solvent | Reaction Temp. | Reaction Time | % Conversion to Products R—H | % Conversion to Products R—R |
|---|---|---|---|---|---|---|
| 1 | p-Chloroanisole | DMF/H₂O (25:1) | 70° | 2 hrs. | (96.8) anisole | (2.5) 4,4'-dimethoxy biphenyl |
| 2 | p-Chloroanisole | DMF/H₂O (50:1) | 70° | 2 hrs. | (88.3) anisole | (11.7) 4,4'-dimethoxy biphenyl |
| 3 | p-Chloroanisole | DMF/H₂O (25:1) | 70° | 1 hr. | (68) anisole | (24) 4,4'-dimethoxy biphenyl |
| 4 | p-Chlorotoluene | DMF/H₂O (25:1) | 70° | 2 hrs. | (92) toluene | (8) 4,4'-dimethyl biphenyl |
| 5 | Chlorobenzene | DMF/H₂O (25:1) | 70° | 2 hrs | (64) benzene | (36) biphenyl |
| 6 | Chlorobenzene | Methanol | 60° | 20 hrs. | (99) benzene | NONE |
| 7 | p-Chlorobenzonitrile | DMF/H₂O (25:1) | 70° | 1 hr. | (90) benzonitrile | (10) 4,4'-dicyano biphenyl |
| 8 | p-Chlorobenzyl-alcohol | DMF/H₂O (25:1) | 70° | 1 hr. | (97) benzyl alcohol | (3) 4,4'-dihydroxymethyl biphenyl |

TABLE-continued

| Example | Organic Halide RX | Solvent | Reaction Temp. | Reaction Time | % Conversion to Products R—H | R—R |
| --- | --- | --- | --- | --- | --- | --- |
| 9 | Triphenylbromomethane | DMF/H$_2$O (50:1) | 60° | 3 hrs. | (100) triphenyl methane | NONE |
| 10 | 1-Bromoadamantane | DMF/H$_2$O (50:1) | 60° | 3 hrs. | (95) adamantane | (5) biadamantane |

EXAMPLE 12

To illustrate that the method is applicable to the reduction of polychlorinated biphenyls (PCB) the following experiment was performed. A 25 ml two-neck flask was charged with 0.03 g NiCl$_2$, 0.5 g triphenylphosphine, 0.25 g NaI and 1.0 g of zinc dust. After the flask was purged with nitrogen, 10 ml of wet DMF was introduced by syringe into the reaction flask. The flask was then placed in an oil bath at 60°, and the reaction mixture was stirred magnetically. When the red-brown catalyst had formed, 100 mg of a commercial Arochlor (a mixture of no less than 20 different chlorinated biphenyls as determined by gas chromatographic analysis) in 1 ml of methanol was added. This mixture was reacted at 60° for four hours. Gas chromatographic analysis of the reaction mixture after this time period revealed that all of the polychlorinated biphenyls had been consumed and had been converted primarily to biphenyl with small amounts of quatraphenyl and other polyphenylenes also present.

To illustrate that metals other than zinc can function in the reduction reaction, the following experiments were performed.

EXAMPLE 13

A 50 ml two-neck flask was charged with 0.13 g of nickel chloride, 0.5 g of sodium iodide, 2.0 g of triphenylphosphine, and 2.0 g of powdered aluminum. Ten ml of DMAC was added to this mixture after a nitrogen atmosphere has been introduced, and the flask was placed in a 60° oil bath. Once the red-brown catalyst had formed, 2 ml of chlorobenzene was added and reacted at 60° for six hours. Analysis of the reaction mixture revealed that all of the chlorobenzene had been consumed and had produced 82% benzene and 18% biphenyl.

EXAMPLE 14

The procedure described in Example 13 was used except that the sodium iodide was omitted from the catalyst mixture, and the reaction time was 20 hours. Gas chromatograph analysis revealed that all of the chlorobenzene had been consumed to produce 77% benzene and 23% biphenyl.

EXAMPLE 15

A 50 ml two-neck flask was charged with 0.13 g of NiCl$_2$, 2.0 g of triphenylphosphine, and 2.0 g of calcium turnings. The catalyst was generated as usual in 10 ml of DMAC, and 2 ml of chlorobenzene were reacted at 60° for 2.5 hours. Gas chromatograph analysis after this time period revealed a yield of 79% benzene and 6% biphenyl with 15% of the chlorobenzene still unreacted.

These examples (13-15) indicate that Al and Ca are better suited to the reduction than zinc. Under conditions where zinc yields primarily coupled products, Al an Ca yield primarily reduced products. They also yield reduced products catalytically without the need for added halide and without a protic solvent.

Although the invention has been described in its preferred forms with a certain degree of particularity, it is understood that the present disclosure has been made only by way of example and that numerous changes can be made without departing from the spirit and the scope of the invention.

What is claimed is:

1. Method of reducing organic halides free of nitro substituents which comprises contacting said organic halides in a solvent under an inert atmosphere with a catalytic amount of a catalytic mixture consisting essentially of:
    (1) a nickel compound containing no radicals in which N and O are bonded directly to each other; and
    (2) a triarylphosphine having 6 to about 24 carbons in each aryl moiety, in the presence of reducing means for maintaining nickel in the zero valence state, at a temperature of up about 250° C., wherein the ratio of triarylphosphine to nickel is at least about 0.1.

2. Method claimed in claim 1 wherein the reducing means is a metal with a greater reduction potential than nickel.

3. Method claimed in claim 2 wherein the metal is aluminum.

4. Method claimed in claim 2 wherein the metal is calcium.

5. Method claimed in claim 2 wherein the metal is magnesium.

6. Method claimed in claim 2 wherein the metal is zinc, the catalyst contains a halide ion wherein the ratio of gram atoms of halide ion to nickel is at least about 0.1 and the solvent contains at least one protic solvent.

7. Method claimed in claim 1 wherein the nickel compound is nickel chloride.

8. Method claimed in claim 1 wherein the triarylphosphine is triphenyl phosphine.

9. Method claimed in claim 6 wherein the halide ion is an iodide.

10. Method claimed in claim 6 wherein the halide ion is bromide ion.

11. Method claimed in claim 6 wherein the solvent is a mixture of a protic solvent and an aprotic solvent.

12. Method claimed in claim 11 wherein the protic solvent is water.

13. Method claimed in claim 11 wherein the aprotic solvent is dimethylformamide.

14. Method claimed in claim 11 wherein the protic solvent is an aliphatic alcohol containing 1 to about 10 carbons.

15. Method claimed in claim 14 wherein the aliphatic alcohol is methanol.

16. Method claimed in claim 1 wherein the organic halide is an aryl halide.

17. Method claimed in claim 16 wherein the aryl halide is an aryl chloride.

18. Method claimed in claim 1 wherein the organic halide is an arylalkyl halide.

19. Method claimed in claim 1 wherein the organic halide is a cycloaliphatic halide.

20. Method claimed in claim 1 wherein the organic halide is a polychlorinated arene.

21. Method claimed in claim 20 wherein the polychlorinated arene is 1,2,4,-trichlorobenzene.

22. Method claimed in claim 20 wherein the polychlorinated arene is a mixture of chlorinated biphenyls.

* * * * *